United States Patent [19]

Utterberg et al.

[11] Patent Number: 5,772,638
[45] Date of Patent: Jun. 30, 1998

[54] PROTECTOR FOR NEEDLE

[75] Inventors: David S. Utterberg, Seattle, Wash.;
William J. Schnell, Livertyville, Ill.

[73] Assignee: Medisystems Technology Corporation, LaVegas, Nev.

[21] Appl. No.: 714,959

[22] Filed: Sep. 17, 1996

[51] Int. Cl.$^6$ .................................................. A61M 5/00
[52] U.S. Cl. ...................... 604/263; 604/171; 604/177; 604/198
[58] Field of Search .................................. 604/171, 177, 604/198, 263, 110, 162, 163, 192

[56] References Cited

U.S. PATENT DOCUMENTS

| | | | |
|---|---|---|---|
| 4,781,692 | 11/1988 | Jagger et al. | 604/164 |
| 4,941,881 | 7/1990 | Masters et al. . | |
| 5,069,341 | 12/1991 | Barbieri et al. | 604/110 X |
| 5,112,311 | 5/1992 | Utterberg et al. . | |
| 5,120,320 | 6/1992 | Fayngold . | |
| 5,330,438 | 7/1994 | Gollobin et al. . | |
| 5,350,368 | 9/1994 | Shields . | |
| 5,562,636 | 10/1996 | Utterberg | 604/263 |
| 5,562,637 | 10/1996 | Utterberg | 604/263 |

FOREIGN PATENT DOCUMENTS 1-212561  2/1988  Japan .

*Primary Examiner*—Sam Rimell
*Assistant Examiner*—Luke J. Yeh
*Attorney, Agent, or Firm*—Gerstman, Ellis & McMillin, Ltd.

[57] ABSTRACT

A medical needle protector sheath having slotted sidewalls to receive a winged needle. The sidewalls define at least one catch projection and preferably one in each sidewall, spaced from closed ends of the slots in the sidewalls, to prevent needle wings occupying the sheath adjacent the closed ends from easily sliding away. The catch projection defines an elongated member having a first end that defines a wing catching tip extending into one of the slots. The elongated member is attached to the sidewall only at an elongated member end that is opposed to the first end. This permits the elongated member to flex in the sidewall plane, providing improved receipt and retention of the needle wings. Also, a protector sheath end wall may be provided that causes a needle and hub to be held in the sheath in an acute angle to the top wall, with the needle tip positioned against the underside of the top wall, a front, upstanding handle may be provided to the protector sheath which is flexible and preferably of substantial C-shape.

28 Claims, 1 Drawing Sheet

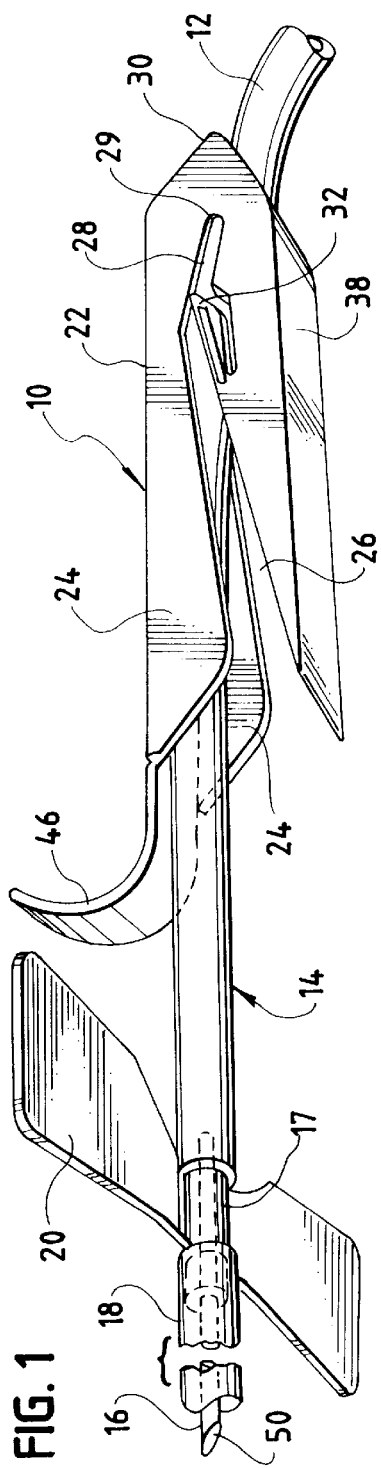
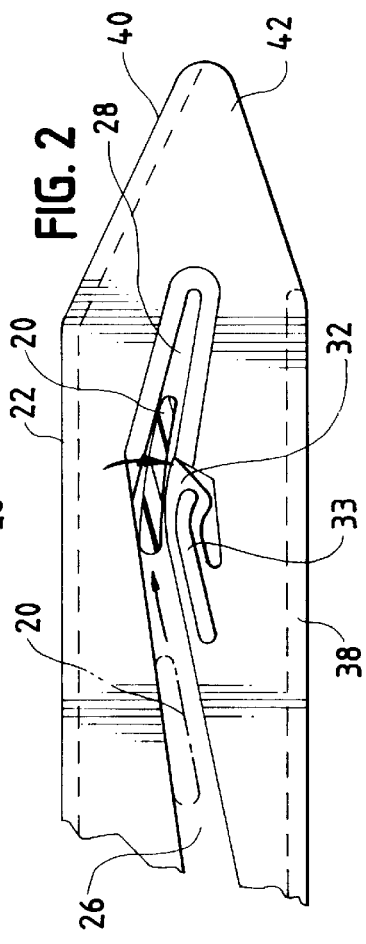
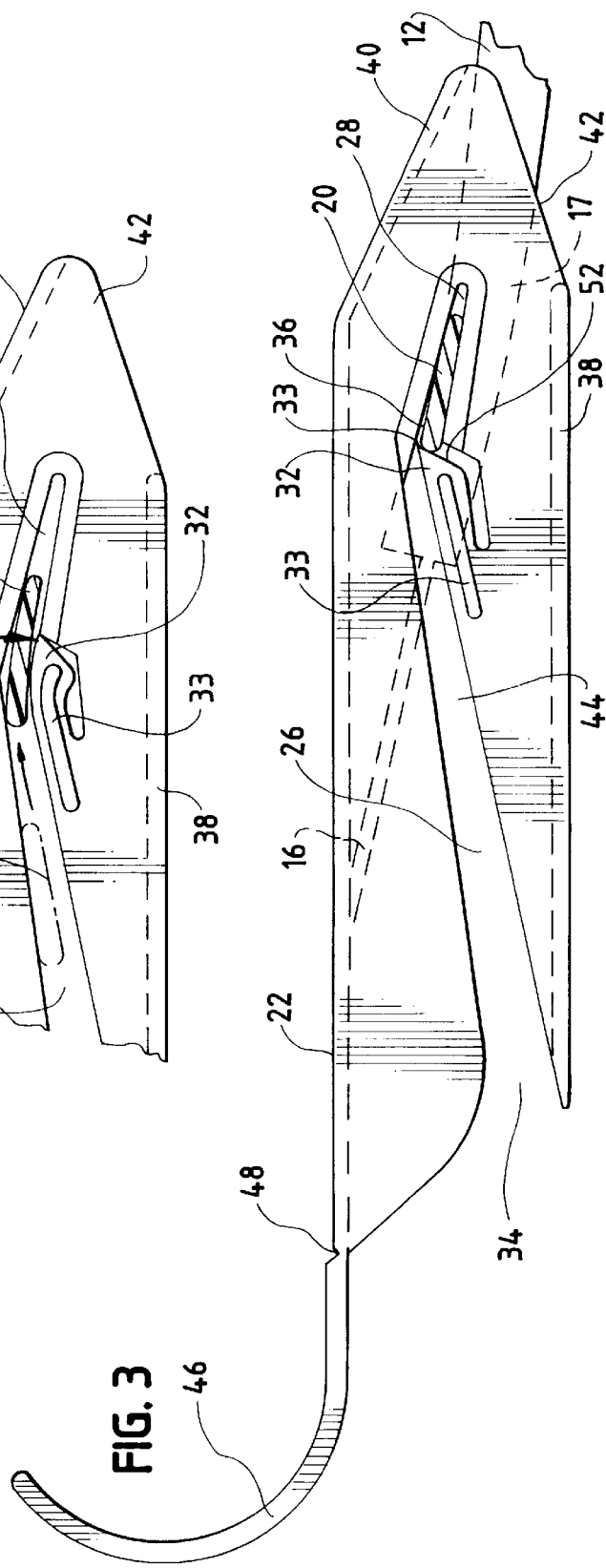

PROTECTOR FOR NEEDLE

BACKGROUND OF THE INVENTION

Many types of needle protector sheaths are known. Particularly, needle protector sheaths for winged needles are clinically used, in which the wings of the needle project outwardly through slits defined in the sheath, so that the sheath can slide from a retracted position to an advanced position while the needle is in use, in which the needle is thus enclosed in the sheath. The sheath is locked in the advanced position, so that the point of the needle is recessed in the sheath and cannot cause accidental injury. For examples of such devices, see Utterberg U.S. Pat. No. 5,112,311; Shields U.S. Pat. No. 5,350,368; Gollobin et al. U.S. Pat. No. 5,330,438; Masters et al. U.S. Pat. No. 4,941,881; Japanese Patent Publication No. 1-212561; and Fayngold U.S. Pat. No. 5,120,320 among others.

One disadvantage of such protector sheaths for needles lies in the fact that it is at least remotely possible for a needle to rotate in a horizontal manner after it has been placed in the sheath, causing a needle tip to project laterally out of one of the slits. This may cause accidental injury. As another issue, clinicians who use the needle protector sheaths wish to make sure that the wings of the needles are securely latched into a rear end portion of the slots as the sheath is advanced so that the sheath will not accidentally retract, again exposing the needle. With earlier designs, some difficulties have been encountered in this.

By this invention one can easily move the needle and wings into a retracted, latched position where the needle tip is securely recessed, while at the same time assuring that the point of the needle is securely retained within the sheath in a position where it cannot shift and project laterally outwardly through one of the slots.

Furthermore, in the use of fistula needles for hemodialysis and the like, some nurses insert the needle into a patient with the bevelled tip of the needle end facing up, and some insert the needle with the bevelled tip down. In many of the prior art needle guards, this can significantly affect the utility of the guard in catching and holding the needle as it is withdrawn from the patient in the customary manner. Most current fistula needle wings project from their hub from a position that is laterally spaced from the center line defining the needle axis. Thus, with many of the prior art slotted needle guards, if a needle has been inserted into a patient with a bevelled needle point up, the wing may pass through the slots of the guard with most of the needle and hub being positioned above the slots (when viewed from the side). However, if the same needle is inserted into a patient with the bevelled needle tip down, then the needle and hub will be positioned mostly below the slot. In each case, of course, the wings will occupy the slot, but the positioning of the rest of the needle and the hub may be substantially changed.

Thus, many of the slotted needle guards of the prior art work poorly for needles and hubs that have been inserted into the patient in an "upside down" manner, from the viewpoint of the design of the prior art slotted guard.

If many of the prior art needle guard sheath configurations were made of a deformable plastic so as to be forgiving as to differences in the dimensions of winged needles, (and particularly the difference in dimensions between a winged needle and the same winged needle in an inverted position) the same flexibility of the sheath housing creates the risk that the prior art catches used to hold the wings of the needle in a retracted position in the sheath may accidentally release the wings through flexing of the housing. Thus, any prior art units that were deformable exhibited a safety problem in that the needle and wings of the winged needle could be accidentally released.

By this invention, a new type of catch is provided, which is more forgiving to flexing of the medical needle protector sheath of this invention, and which more reliably holds the wings of needles, thus preventing them from being accidentally removed from the sheath or accidentally allowing the needle point to project laterally outward through the slots.

Furthermore, the prior art needle sheaths often utilize an "anchor" as typically taught in Utterberg et al. U.S. Pat. No. 5,112,311. In the field of dialysis, when a winged fistula needle is to be removed, the nurse presses the site of needle entry with a wad of gauze, while bringing the needle sheath up to a position where one of her fingers can press on or otherwise grasp the forwardly projecting "anchor". Then, the nurse pulls the needle tubing, causing the needle to withdraw and to retract back into locked relation with the slotted sheath, while the sheath is prevented from retraction by the manual pressure on the anchor. At this moment, the nurse does not want to reduce finger pressure on the gauze, which is preventing bleeding at the needle access point. In the prior art, this means that the nurse cannot conveniently release the anchor so that the needle and set can be removed without a reduction in finger pressure.

By this invention, the advantages of an anchor on the slotted sheath may be achieved, but at the same time the sheath and needle may be removed without the nurse letting up on the finger pressure on the gauze.

Furthermore, the protector sheath of this invention holds the needle in a locked relation in which the needle extends upwardly into substantial engagement with the top wall of the sheath. This puts the tip of the needle in vertically spaced relation to the slots in the sidewalls, providing further assurance that the needle tip cannot project out of a sidewall. This can be facilitated by the use of an end wall which extends downwardly part of the distance from the top wall toward a bottom wall of the sheath, forcing the needle hub and tubing downwardly, rather in a pivoting relation about the wings in slot portions of the sheath, which, in turn, forces and holds the needle tip up.

DESCRIPTION OF THE INVENTION

By this invention, a medical protector sheath comprises a body having a top wall, sidewalls, a slot formed in each sidewall to receive a needle wing extending through each of said slots, and at least partially open ends. The slots each define first portions, each having one closed end, positioned adjacent to one end of the body. The sidewalls define at least one catch projection, which is spaced from the closed ends of the slots, to prevent needle wings that occupy the first slot portions from easily sliding away from the first slot portions. The catch projection defines an elongated member having a first end that defines a wing catching tip extending into one of the slots. The elongated member is attached to the sidewall only at an elongated member end that is opposed to the first end, to permit the elongated member to flex in the sidewall plane. Also, the elongated member preferably extends into a direction that defines an acute angle to at least the majority of the top wall, with the first end facing the first slot portion.

Preferably, the wing catching tip of the elongated member is either in contact with the upper surface of the slot or in close proximity thereto. Particularly, it is preferred for the elongated member to be spaced, in its normal, unflexed position, from the slot upper edge by a distance which is less than the thickness of the needle wings that the sheath is designed to retain.

Preferably the first slot portions extend at an acute angle away from the top wall from the vicinity of the elongated members to the closed slot ends. The sheath may further comprise a bottom wall, and an end wall at the one body end which is adjacent to the slot closed end portions. The end wall extends from the vicinity of the top wall downwardly to a position above the bottom wall. As a result of this, the needle and hub may be held in the sheath at an acute angle to the top wall when the wings occupy the first slot portions.

Also, portions of the slots which are more remotely spaced from the end wall than the elongated member may extend from the vicinity of the elongated member in an acute angle away from the top wall to open slot ends at the needle protector sheath end which is opposed to the one end.

The sheath may also have a flexible, upstanding handle which is preferably of C-shape, for manual retention of the sheath. This handle may project from the top wall adjacent the end of the sheath which is opposed to the one end. Also, the handle may communicate with the top wall of the sheath through a line of flexing weakness, to facilitate the flexibility of the handle. Thus the user, while withdrawing a winged needle into the sheath, may hold the upstanding handle with a finger. The handle may have sufficient stiffness to permit the needle to be pulled into the sheath and locked therein, but the handle is sufficiently flexible so that the sheath may be removed from the finger that the handle engages by flexing without a need to move the finger.

The sheath may also be made of a flexible plastic so that it can receive and hold winged needles of a variety of shape configurations, which includes, as previously discussed, needles which are of differing dimension relative to the plane of the wings, when inverted. Also, the elongated member may carry a longitudinal strengthening rib.

Thus a needle-receiving sheath is provided by this invention which exhibits significant improvements over the corresponding sheaths of the prior art.

DESCRIPTION OF THE DRAWINGS

In the drawings, FIG. 1 is a perspective view of a needle sheath of this invention, carried on a fistula set for hemodialysis;

FIG. 2 is an enlarged elevational view of the first or back end of the sheath, showing how a wing of the needle, shown in section, can move to the first slot portion adjacent the one end of the body; and FIG. 3 is an enlarged elevational view of the complete protector sheath, showing how the wing of the needle is held in position within the first slot portion by the catch projection.

DESCRIPTION OF SPECIFIC EMBODIMENTS

Referring to the drawings, medical needle protector sheath 10 is shown to be carried on tubing 12 of a conventional winged needle fistula set 14, having a needle 16, closed with a removable needle guard 18, and having wings 20 projecting outwardly from hub 17.

The tubing 12 can be seen to be extending entirely through the hollow interior of protector sheath 10.

Protector sheath 10 comprises a body having a top wall 22, sidewalls 24, and a slot 26 formed in each sidewall to receive a needle wing 20 as the needle is retracted from the patient rearwardly into protector sheath 10 and held there by latching of the wings.

The respective slots 26 define first slot portions 28, each of the first slot portions having one closed end 29 adjacent one end 30 of the body of sheath 10.

The respective sidewalls 24 each define a catch projection 32, each of which is spaced from the respective closed end 29 of slot portion 28, and which serves to prevent needle wings that occupy first slot portions 28 from easily sliding away from the first slot portions. Catch projections 32 are also sufficiently flexible, as particularly shown in FIG. 2, to be deflected downwardly as the respective needle wings 20 slide from the open mouth 34 of slots 26, along the slots, to enter the first slot portions 28 by deflection of catch projections 32 as in FIG. 2. Then, as shown in FIG. 3, catch projections 32 can spring back into their original configuration in which a wing catching tip 33 of the catch projection 32 is either in contact with the upper surface 36 of slot 28 or in close proximity thereto, less than the thickness of the wings 20. Thus, as FIG. 3 illustrates, the respective wings 20 are not easily removed from their occupancy of the first slot portions 28 once they have entered the first slot portions. Thus, the sharp point of needle 16 is also retained within the protector sheath, typically being pressed against the underside of top wall 22 because the first slot portions 28 extend at an acute angle away from top wall 22 from the vicinity of elongated members 32 to the closed ends 29, as shown in phantom lines 16 in FIG. 3. Typically this acute angle is about 5 to 20 degrees.

Elongated member 32 may carry a longitudinal strengthening rib 33.

Sheath 10 also comprises a bottom wall 38 and an end wall 40 at and adjacent the one body end 30. End wall 40 extends from the vicinity of top wall 22 downwardly in an angled manner to a position above bottom wall 38, so that an aperture 42 is provided in a lower portion of the sheath, through which tubing 12 can extend. However, as shown particularly in FIG. 1, tubing 12 is thus forced downwardly, away from top wall 22, which, in turn, facilitates the forcing of the needle 16 to upwardly rotate at flexible wings 20, to assure an upward position of needle 16 as shown in FIG. 3 so that the sharp point is well out of harm's way, and also to prevent the sharp needle point from accidentally projecting outwardly through one of slots 26.

The remaining portions 44 of slots 26, which are more remotely spaced from end wall 29 than elongated member 32, may extend from the vicinity of elongated member 32 in an acute angle away from top wall 22 to the open slot ends 34. Typically, this acute angle is also about 5 to 20 degrees, as is the corresponding acute angle of first slot portion 28.

At the end of the sheath which is opposed to first end 30, an integral, flexible, upstanding handle 46 may be carried, for manual retention of the sheath. The flexibility of handle 46 may be enhanced by the presence of a transverse line of flexing weakness 48.

The medical needle protector sheath of this invention may comprise a single, integrally molded piece made of a plastic which is somewhat flexible at the dimensions used. Thus, as previously described, the sheath can be used with winged needles in which the wings 20 are spaced from the longitudinal axis of the set as defined by the axis of needle 16 irrespective of whether the needle and set are in use with the bevelled tip 50 facing downwardly as shown in FIG. 1 or in an inverted position where the bevelled tip 50 faces upwardly. The flexibility of sheath 10 can accommodate the differing dimensions or location of the wings in these two circumstances because of the design of the elongated member 32 of the catch projection, as shown. The front surface 52 of elongated member 32 is angled slightly forwardly from bottom to top so that when wing 20 is attempted to be retracted along the slots toward their mouths 34, the elongated member 32 of the catch projection is forced upwardly by the wing to engage the upper wall 36 of slot portion 28. Thus, no amount of pulling, apart from destruction, can cause wings 20 to be dislodged out of their locked position, and this situation continues to hold even when the sheath is twisted, opened, or otherwise manually deformed.

Accordingly, as taught in Utterberg U.S. Pat. No. 5,112, 311, the fistula needle 16 is positioned in the vein of a patient, and the wings are strapped to the skin. For removal of the fistula needle, the wings are released from their adhesive tape straps; a wad of gauze is placed on the puncture site of the needle to the skin; and the nurse presses the gauze on that point while hooking one finger around upstanding handle 46. Then, the nurse simply pulls on tubing 12 to withdraw needle 16, causing the needle and wings to retract back into protector sheath 10, with the wings 20 sliding through slots 26. The acute angle of slot 26 is present to match the approximate angle of needle 16 to the skin the patient, so that the needle is not twisted as it is withdrawn. Then, as the needle continues to be withdrawn, sliding through slots 26, the wings 20 depress elongated member 32 of the catch projection, permitting the wings to slide into first slot portions 28. When the wings arrive in first slot portions 28, catch projections 32 spring back to their original position, as shown in FIG. 3, firmly and reliably retaining wings 20 in the position of occupying first slot portion 28. Simultaneously, since first slot portion 28 occupies an acute angle of opposite sense to the acute angle of the rest of slot 26, and also because of the presence of wall 40 that forces tube 12 downwardly, needle 16 is forced to rotate upwardly so that the tip impacts against the lower surface of wall 22, where it is firmly held out of harm's way.

The above is offered for illustrative purposes only, and is not intended to limit the scope of the invention of this application, which is as defined in the claims below.

That which is claimed is:

1. A medical needle protector sheath which comprises a body having a top wall, sidewalls, a slot formed in each sidewall to receive a needle wing extending through each of said slots, said slots each defining first slot portions, each having one closed end adjacent one end of said body, said sidewalls defining at least one catch projection spaced from said closed ends of said slots to prevent needle wings that occupy said first slot portions from easily sliding away from said first slot portions, said catch projection defining an elongated member having a length greater than its width and having a first, free end that defines a wing catching tip extending into one of said slots, said elongated member being attached to the sidewall only at an elongated member end that is opposed to said first end, to permit said elongated member to flex in the sidewall plane, and further in which said elongated member extends in a direction that defines an acute angle to at least the majority of said top wall, with the first end of the elongated member facing said first slot portion.

2. The sheath of claim 1 in which said first slot portions extend at an acute angle away from said top wall from the vicinity of said elongated members to said closed ends.

3. The sheath of claim 1 which further comprises a bottom wall and an end wall at the one body end adjacent said slot closed end portions, said end wall extending from the vicinity of said top wall downwardly to a position above the bottom wall, whereby said needle and hub may be held by said end wall in the sheath at an acute angle to said top wall when the wings occupy the first slot portions.

4. The sheath of claim 3 in which said end wall extends diagonally outward from said top wall.

5. The sheath of claim 3 in which portions of said slots which are more remotely spaced from said end wall than said elongated member extend from the vicinity of said elongated member in an acute angle away from said top wall to open slot ends at the needle protector sheath end which is opposed to said one end.

6. The sheath of claim 1 in which a flexible, upstanding handle for manual retention of said sheath projects from said top wall adjacent the end of said sheath which is opposed to said one end.

7. The sheath of claim 6 in which said handle is substantially of C-shape.

8. The sheath of claim 6 in which said handle communicates with said top wall through a line of flexing weakness to facilitate the flexibility of said handle, whereby the user, while withdrawing a winged needle into the sheath, may hold the upstanding handle with a finger, and the handle has sufficient stiffness to permit the needle to be pulled into the sheath and locked therein, but the handle is sufficiently flexible so that the sheath may be removed from the finger that the handle engages by flexing without a need to move the finger.

9. The sheath of claim 1, which is made of a flexible plastic, to receive and hold winged needles of a variety of shape configurations.

10. The sheath of claim 1, in which the wing catching tip extends toward a top wall of said slot, to be in contact with said top wall or spaced therefrom by a distance which is less than the thickness of needle wings occupying said first slot portions.

11. The sheath of claim 1, in which said elongated member carries a longitudinal strengthening rib.

12. A medical needle protector which comprises a body having a top wall, sidewalls, a slot formed in each sidewall to receive a needle wing extending through each of said slots, said slots each having one at least partially open end, said slots each defining first slot portions, each first slot portion having one closed end adjacent one end of said body, said sidewalls defining at least one catch projection spaced from said closed ends to prevent needle wings that occupy said first slot portions from easily sliding away from said first slot portions, said catch projection defining an elongated member having a first end that defines a wing catching tip extending into one of said slots, said elongated member being attached to the sidewall only at an elongated member end that is opposed to said first end, to permit said elongated member to flex in the sidewall plane, said sheath further comprising a bottom wall and an end wall at said one body end adjacent said slot closed ends, said end wall extending from the vicinity of said top wall downwardly to a position above the bottom wall, whereby said needle and hub may be held by said end wall in the sheath at an acute angle to said top wall when the wings occupy said first slot portions.

13. The sheath of claim 12 in which said first slot portions extend at an acute angle away from said top wall from the vicinity of said elongated members to said slot closed ends.

14. The sheath of claim 13 in which portions of said slots which are more remotely spaced from said end wall than said elongated member extend from the vicinity of said elongated member in an acute angle away from said top wall to open slot ends at the needle protector sheath end which is opposed to said one end.

15. The sheath of claim 14 in which a flexible, upstanding handle for manual retention of said sheath projects from the top wall adjacent to the end of said sheath which is opposed to said one end.

16. The sheath of claim 15 in which said handle is substantially C-shaped.

17. The sheath of claim 15 in which said handle communicates with said top wall through a line of flexing weakness to facilitate flexibility of said handle, whereby the user, while withdrawing a winged needle into the sheath, may hold the upstanding handle with a finger, and the handle has sufficient stiffness to permit the needle to be pulled into the sheath and locked therein, but the handle is sufficiently flexible so that the sheath may be removed from the finger that the handle disengages by flexing without a need to substantially move the finger.

18. The sheath of claim 17 which is made of a flexible plastic, to receive and hold winged needles of a variety of shape configurations.

19. The sheath of claim 18 in which the wing catching tip extends towards a top wall of said slot, to be in contact with said top wall or spaced therefrom by a distance which is less than the thickness of needle wings occupying said first slot portions.

20. The sheath of claim 19 in which said elongated member carries a longitudinal strengthening rib.

21. The sheath of claim 19 in which said elongated member extends in the direction that defines an acute angle to at least the majority of said top wall, with the first end facing said first slot portion.

22. The medical needle protector sheath which comprises a body having a top wall, sidewalls, a slot formed in each sidewall to receive a needle wing extending through each of said slots, said slots each having one at least partially open end, said slots each defining first slot portions having one closed end adjacent one end of said body, said sidewalls defining at least one catch projection spaced from said closed slot ends to prevent needle wings that occupy said first slot portions from easily sliding away from said first slot portions, said catch projection defining an elongated member having a length greater than its width and having a first, free end that defines a wing catching tip extending into one of said slots, said elongated member being attached to the sidewall only at an elongated member end that is opposed to said first end, to permit said elongated member to flex in the sidewall plane, said elongated member also extending in a direction that defines an acute angle to at least the majority of said top wall, with the first end facing said first slot portion, said first slot portions also extending at an acute angle away from said top wall from the vicinity of said elongated members to said closed ends, portions of said slots which are more remotely spaced from said closed ends than said elongated member extending from the vicinity of said elongated member in an acute angle away from said top wall to said open slot ends at the needle protector sheath end which is opposed to said one end.

23. The sheath of claim 22 in which a flexible, upstanding handle for manual retention of said sheath projects from said top wall adjacent the end of said sheath which is opposed said one end.

24. The sheath of claim 23 in which said upstanding handle is substantially C-shaped, said handle having sufficient flexibility and strength whereby the user, while withdrawing a winged needle into the sheath, may hold the upstanding handle with a finger, and the handle has sufficient stiffness to permit the needle to be pulled into the sheath and locked therein, but the handle is sufficiently flexible so that the sheath may be removed from the finger that the handle engages by flexing without a need to substantially move a finger.

25. The sheath of claim 24 in which made of a flexible plastic, to receive and hold winged needles of a variety of shape configurations.

26. A medical needle protector sheath which comprises a body having a top wall, sidewalls, a slot formed in each sidewall to receive a needle wing extending through each of said slots, said slots each defining first slot portions, each having one closed end adjacent one end of said body, said sidewalls defining at least one catch projection spaced from said closed ends to prevent needle wings that occupy said first slot portions from easily sliding away from said first slot portions, said catch projection defining an elongated member having a first end that defines a wing catching tip extending into one of said slots, said elongated member being attached to the sidewall only at an elongated member end that is opposed to said first end, to permit said elongated member to flex in the sidewall plane, and further in which said elongated member extends in a direction that defines an acute angle to at least the majority of said top wall, with the first end of the elongated member facing said first slot portion, and in which said elongated member carries a longitudinal strengthening rib.

27. The sheath of claim 26 which further comprises a bottom wall, and an end wall at the one body end adjacent said slot closed end portions, said end wall extending from the vicinity of said top wall downwardly to a position above said bottom wall, whereby said needle and hub may be held by said end wall in the sheath at an acute angle to said top wall when the wings occupy the first slot portions so that the needle has a tip which engages the top wall.

28. The sheath of claim 27 which is made of a flexible plastic, to receive and hold winged needles of a variety of shape configurations.

* * * * *